United States Patent [19]

Nutt et al.

[11] Patent Number: 5,091,366
[45] Date of Patent: Feb. 25, 1992

[54] PEPTIDES HAVING ANF ACTIVITY

[75] Inventors: Ruth F. Nutt, East Greenville; Terrence M. Ciccarone, Harleysville; Stephen F. Brady, Philadelphia; Daniel F. Veber, Ambler, all of Pa.

[73] Assignee: Merck & Co., Inc., Rahway, N.J.

[21] Appl. No.: 534,001

[22] Filed: Jun. 4, 1990

Related U.S. Application Data

[63] Continuation of Ser. No. 403,999, Sep. 5, 1989, abandoned, which is a continuation of Ser. No. 51,981, May 19, 1987, abandoned.

[51] Int. Cl.$^5$ .................. C07K 7/64; A61K 37/02
[52] U.S. Cl. .................. 514/11; 530/326; 530/327; 530/321; 530/317; 514/13; 514/14; 930/DIG. 553
[58] Field of Search ........... 530/326, 317, 327, 321; 514/13, 14, 11

[56] References Cited

U.S. PATENT DOCUMENTS 4,670,540 6/1987 Sakakibara .................. 530/326

OTHER PUBLICATIONS

Dayoff, M., *Atlas of Protein Sequence and Structure*, vol. 5, 89–99, 1972.

Kohzuhi, M. et al., *Chem. Abs.*, 110:152096p, 1989.
Raine, A. et al., *New England Journal of Medicine*, 315(9):533–537, 1986.
Edwards, B. et al., *Cardiovascular Drugs and Therapy*, 1:89–100, 1987.
Tsunoda et al., *Chem. Abs.*, 108:92513u, 1988.
Kiso et al., *Peptides: Struc. and Function*, Proc. of the 9th Am. Peptide Symp., Ed. Deber, Kapple, 1985.
PCT/WO8 7/02674, published 7.5.87, Lewieki, pp. 97–123.
Kiso, Y. et al., Peptides: Struc. and Func., Proceeding of 9th Am. Pept. Symp., Pierce Chem. Co., 949–952, 1985.

*Primary Examiner*—Howard E. Schain
*Assistant Examiner*—Susan M. Perkins
*Attorney, Agent, or Firm*—Frank P. Grassler; Donald J. Perrella; Hesna J. Pfeiffer

[57] ABSTRACT

Analogs of the 17-membered ring portion of ANF wherein the cysteine moiety is replaced with dipeptidyl moieties, specifically, Phe-Pro, NMP-Pro, Pro-Pro, Val-Pro, Lys-Pro, Ile-Pro, Arg-Pro, HAr-Pro, Dly-Pro, Arg-Pro, Lys-BAr, Arg-Pro, CyA-CyA, Cys-Cys, or with α-aminoheptanoic acid result in analogs of ANF having increased potencies and metabolic stability.

6 Claims, No Drawings

PEPTIDES HAVING ANF ACTIVITY

This is a divisional application Ser. No. 07/403,999 filed Sept. 5, 1989, which is a continuation of Ser. No. 07/081,981 now both abandoned.

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297–302, 1983) and atriopeptin (Currie et al., Science 111: 67, 1984).

DESCRIPTION OF EARLIER ARTICLES AND PATENTS

Thibault et al., FEBS Lett. 164 (2): 286–290 (1983), discloses three peptides of 26, 31 and 33 amino acids and gives their amino acid composition but does not give any amino acid sequences. Since these peptides were isolated from rat atria, all optically active amino acids have L-configuration.

Flynn et al., Biochem. Biophys. Res. Comm. 117 (3): 859–865 (1983), discloses a 28-amino acid

```
 6    7    8    9   10   11
Ser—Leu—Arg—Arg—Ser—Ser—
12   13   14   15   16   17   18   19   20   21
Cys—Phe—Gly—Gly—Arg—Ile—Asp—Arg—Ile—Gly—
 |
22   23   24   25   26   27   28   29   30   31
Ala—Gln—Ser—Gly—Leu—Gly—Cys—Asn—Ser—Phe—
32   33
Arg—Tyr.
```

Since this peptide was isolated from rat atria, all optically active amino acids have L-configuration.

Currie et al., Science 223: 67–69 (1984), disclose two peptides having sequences 10–30 and 10–32 (numbering as above). Since these peptides were isolated from rat atria, all optically active amino acids have L-configuration.

Kangawa et al., Biochem. Biophys. Res. Comm. 118 (1): 131–139 (1984), disclose a 28-amino acid peptide having sequence 6–33 (numbering as above) having a methionine residue in lieu of isoleucine in 17-position. Since this peptide was isolated from atrial tissue, all optically active amino acids have L-configuration.

Thibault et al., FEBS Lett. 167 (2): 352–357 (1984), disclose isolation of a peptide of 103 amino acids and give the sequence of the C-terminal 73-amino acid fragment. The three peptides disclosed by Thibault et al., supra, correspond to C-terminal fragments of this peptide. Since all of these peptides were isolated from rat atria, and one that was synthesized conformed to the shortest one isolated, all optically active amino acids have L-configuration.

Misono et al., Biochem. Biophys. Res. Comm. 119 (2): 524–529 (1984), disclose isolation of a 25-amino acid peptide of sequence 9–33 (numbering as above). Since this peptide was isolated from rat atria, all optically active amino acids have L-configuration.

Needleman et al., U.S. Pat. No. 4,496,544, discloses isolation from several peptides of sequences 12–29, 12–30, 12–32, 12–33, 11–29, 11–30, 11–32, 11–33, 10–29, 10–30, 10–32 and 10–33 (numbering as above). Since all of these peptides were isolated from rat atria, all optically active amino acids have L-configuration.

OBJECTS OF THE INVENTION

It is an object of the present invention to provide novel peptides having activity like that of ANF peptides isolated from biological materials. Another object is to provide novel peptides having potent natriuretic, vasodilatory and hypotensive activity. A further object is to provide novel peptides having enhanced metabolic stability. These and other objects of the present invention will be apparent from the following description.

SUMMARY OF THE INVENTION

Novel peptides having potent natriuretic activity are disclosed with the following amino acid sequence:

$$X-A-B-C-D-E-F-G$$
$$| \qquad\qquad\qquad\qquad\quad \diagdown H$$
$$Y-(O)_n-N-M-L-(K)_n-(J)_n-I \diagup$$

wherein
X is Pro,
Y is Phe, Pro, Val, Ile, NMP, Lys, Arg or hAr,
and X-Y together is AHa, Cys-Cys, or CyA-CyA.
A is Phe, OMT or ChA;
B is Gly, DAl or DPh;
C is Gly or Ala;
D is DAr, Arg, Pro or DLy or Lys;
E is Ile, Met, MeO, MO2, Leu, Nle or Val;
F is Asp, Glu, Aib, αMA or αMG;
G is Arg or Lys;
H is Ile or Val;
I is Gly, Aib, D- or L-Ala;
J is Ala, NMA, Phe, NMP or Pro;

K is DGl, Gln, DAl or Ala;
L is Ser, His, Arg or Lys;
M is Gly, DAl, Ala or Pro;
N is Leu, Phe or ChA; and
O is Gly, DAl, Ala, DAr, Arg, hAr, hDA, DLy or Lys; and
n is 0 or 1,
and the amides, lower alkyl esters and the physiologically acceptable metal salts and acid addition salts thereof.

DETAILED DESCRIPTION

It has now been found that the foregoing peptides have properties similar to those of ANF peptides isolated from biological materials, e.g., potent natriuretic, vasodilatory and hypotensive activity, but with increased potency and metabolic stability.

In the present specification, the following abbreviations will be used for the indicated amino acid. Unless indicated otherwise all optically active amino acids have the L-configuration.

| | |
|---|---|
| αMA | α-methylaspartic acid |
| αMG | α-methylglutamic acid |
| Aha | aminoheptanoic acid |
| Aib | aminoisobutyric acid |
| Ala | alanine |
| Arg | arginine |
| Asp | aspartic acid |
| BAr | Boc-Arg |
| BDA | Boc-D-Arg |
| ChA | cyclohexylalanine |
| CyA | acetamidocysteine |
| DAl or D-Ala | D-alanine |
| DAr or D-Arg | D-arginine |
| DGl or D-Gln | D-glutamine |
| DLy or D-Lys | D-lysine |
| DPh or D-Phe | D-phenylalanine |
| Gln | glutamine |
| Glu | glutamic acid |
| Gly | glycine |
| hAr | homo-arginine |
| hDA | homo-D-arginine |
| His | histidine |
| Ile | isoleucine |
| Leu | leucine |
| Lys | lysine |
| Met | methionine |
| MeO | methionine sulfoxide |
| MO2 | methionine sulfone |
| Nle | norleucine |
| NMA | N-methylalanine |
| NMP | N-methylphenylalanine |
| OMT | O-methyltyrosine (p-methoxyphenylalanine) |
| Phe | phenylalanine |
| Pro | proline |
| Ser | serine |
| Val | valine |

The polypeptides of the present invention and the salts thereof can be manufactured according to known synthetic methods elongating the peptide chain, i.e. by condensing amino acids stepwise or coupling the fragments consisting of two to several amino acids, or by combination of both processes, or by solid phase synthesis according to the method originally described by Merrifield, J. Am. Chem. Soc. 85:2149–2154 (1963). Alternatively, the peptides of the present invention may be synthesized using automated peptide synthesizing equipment.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, N-hydroxysuccinic acid imido ester method, cyanomethyl ester method, etc), Woodward reagent K method, carbonyldiimidazol method, oxidation-reduction method. These condensation reactions may be done in either liquid phase or solid phase. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

As is usual in peptide synthesis, it is necessary to protect/deprotect the α- and ω- side chain amino groups and the carboxy group of the amino acid as occasion demands. The applicable protective groups to amino groups are exemplified such as benzyloxycarbonyl (hereinafter abbreviated as Z), o-chlorobenzyloxycarbonyl [Z(2-Cl)], p-nitrobenzyloxycarbonyl [Z(NO₂)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), 4-nitrobenzyl ester (ONb), t-butyl ester (OBut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluene-sulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenylsulfonyl (Mts), and the like. The thiol group in cysteine may be protected with benzyl, p-methoxybenzyl, triphenylmethyl, acetylaminomethyl, ethylcarbamoyl, 4-methylbenzyl, 2,4,6-trimethylbenzyl (Tmb) etc, and the hydroxyl group in serine can be protected with benzyl, t-butyl, acetyl, tetrahydropyranyl etc.

Some preferred compounds of the present invention have the following amino acid composition

| | X | Phe | B | C | Arg | Ile | F | Arg | Ile | I | J | Gln | Ser | M | Leu | O | Y |
|---|---|---|---|---|---|---|---|---|---|---|---|---|---|---|---|---|---|
| 1. | Pro | Phe | Gly | Gly | Arg | Ile | Asp | Arg | Ile | Gly | Ala | Gln | Ser | Gly | Leu | Gly | Phe |

-continued

| | | | | | | | | | | | | | | | | |
|---|---|---|---|---|---|---|---|---|---|---|---|---|---|---|---|---|
| 2. | " | " | " | " | " | " | Glu | " | " | " | " | " | " | " | " | " |
| 3. | " | " | " | " | " | " | " | " | " | " | " | " | " | " | Arg | " |
| 4. | " | " | " | " | " | " | " | " | " | " | " | " | " | " | DAr | " |
| 5. | " | " | " | DPh | Ala | " | " | " | " | Ala | Phe | " | " | Pro | " | Ala | " |
| 6. | CyA | " | " | Gly | Arg | " | " | " | " | Gly | Ala | " | " | Gly | " | Gly | CyA |
| 7. | Cys<br>\|<br>S | " | " | " | " | " | " | " | " | " | " | " | " | " | " | Cys<br>\|<br>S |
| 8. | Phe | " | " | " | " | Asp | " | " | " | " | " | " | " | " | " | Gly |
| | └─── Aha ───────────────────────────────────────┘ | | | | | | | | | | | | | | | |

Other compounds of the present invention are the following:

| | | | | | | | | | | | | | | | | |
|---|---|---|---|---|---|---|---|---|---|---|---|---|---|---|---|---|
| 8. | Pro | TyM | DAl | Gly | LAr | Met | Aib | Lys | Val | Aib | NMP | Gln | Ser | Pro | Leu | Ala | Pro |
| 9. | Val | ChA | DPh | Ala | Pro | MeO | αMA | Arg | Ile | DAl | NMA | " | " | " | " | " | " |
| 10. | CyA | Phe | Gly | Gly | Arg | Ile | Asp | Arg | Ile | Gly | Ala | Gln | Ser | Gly | Leu | Gly | CyA |
| 11. | Pro | " | " | " | " | " | " | " | " | " | " | — | " | " | " | " | Ile |
| 12. | " | " | " | " | " | " | " | " | " | " | " | Gln | " | " | " | DAr | NMP |
| 13. | " | " | " | " | " | " | " | " | " | " | " | " | " | " | " | — | Lys |
| 14. | " | " | " | " | " | " | " | " | " | " | " | " | " | " | " | Arg | Arg |
| 15. | " | " | " | " | " | " | " | " | " | " | " | — | " | " | " | " | hAr |
| 16. | " | " | Dal | Ala | DAr | MO2 | Aib | Lys | Val | Ala | Pro | DGl | His | Ala | Phe | DAl | Phe |
| 17. | " | OMT | " | " | Pro | Leu | αMA | " | " | " | " | " | " | " | " | " | " |
| 18. | " | ChA | DPh | Gly | Lys | Nle | αMg | " | " | Aib | "DAl | Arg | DAl | ChA | Ala | " | |
| 19. | " | " | " | " | Dly | Val | Aib | " | " | DAl | " | " | Lys | " | " | " | " |
| 20. | " | " | " | " | " | " | " | " | " | " | " | " | " | " | " | hAr | Ile |
| 21. | " | " | " | " | " | " | " | " | " | " | " | " | " | " | " | hDA | " |
| 22. | " | " | " | " | " | " | " | " | " | " | " | " | " | " | " | Lys | " |
| 23. | " | " | " | " | " | " | " | " | " | " | " | " | " | " | " | Dly | " |

One method of preparing the compounds of the present invention is illustrated by the following example wherein a protected peptide of the formula

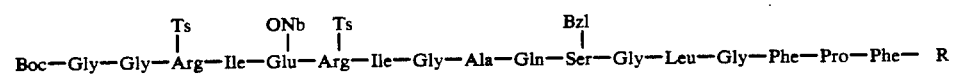

Boc—Gly—Gly—Arg(Ts)—Ile—Glu(ONb)—Arg(Ts)—Ile—Gly—Ala—Gln—Ser(Bzl)—Gly—Leu—Gly—Phe—Pro—Phe— R is treated with HF and anisole to yield a peptide of the formula

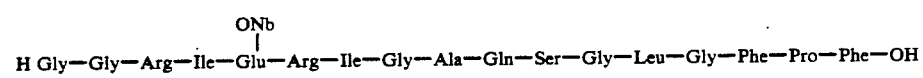

H Gly—Gly—Arg—Ile—Glu(ONb)—Arg—Ile—Gly—Ala—Gln—Ser—Gly—Leu—Gly—Phe—Pro—Phe—OH

The latter peptide then is treated with 1-ethyl-3-(3-dimethylaminopropyl)carbodiimide-hydroxybenz-triazole and triethylamine to yield the cyclic protected peptide of the formula

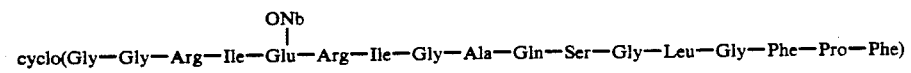

cyclo(Gly—Gly—Arg—Ile—Glu(ONb)—Arg—Ile—Gly—Ala—Gln—Ser—Gly—Leu—Gly—Phe—Pro—Phe)

The latter in turn is treated with H$_2$/Pd/C or Zn/HOAc to yield the deprotected cyclic peptide of the formula
cyclo(Gly-Gly-Arg-Ile-Glu-Arg-Ile-Gly-Ala-Gln-Ser-Gly-Leu-Gly-Phe-Pro-Phe)

What is claimed is:
1. A peptide having the amino acid sequence:

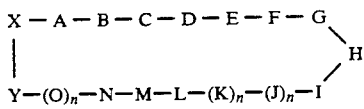

wherein
X is Pro;
Y is Phe, Pro, Val, Ile, NMP, Lys, Arg, or hAr
A is Phe, OMT or ChA;
B is Gly, D-Ala or D-Phe;
C is Gly or Ala;
D is D-Arg, Arg, Pro, D-Lys or Lys;
E is Ile, Met, MeO, MO2, Leu, Nle or Val;
F is Asp, Glu, Aib, α-MA or α-MG;
G is Arg or Lys;
H is Ile or Val;
I is Gly, Aib, D-Ala or Ala;
is Ala, NMA, Phe, NMP or Pro;
K is D-Gln, D-Ala or Ala;
L is Ser, His, Arg or Lys;
M is Gly, D-Ala, Ala or Pro;
N is Leu, Phe or ChA;
O is Gly, D-Ala, Ala, D-Arg, Arg, hAr, hDA, D-Lys, or Lys;
n is 0 or 1;
and the amides, lower alkyl esters and the physiologically acceptable metal salts and acid addition salts thereof.

2. A peptide having the amino acid sequence:

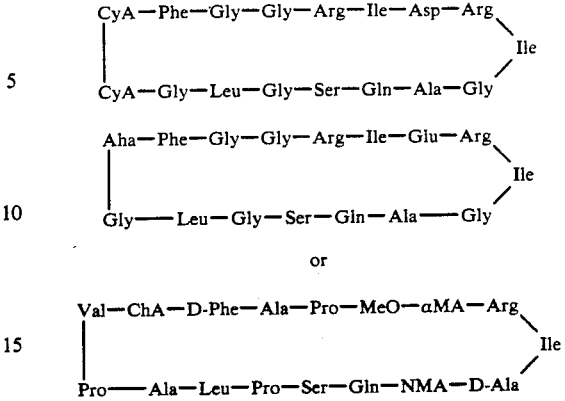

3. A natriuretic composition comprising a peptide of claim 1 in combination with a pharmaceutically acceptable carrier.

4. A method of lowering hypertension which comprises administering to a mammalian species a therapeutically active amount of a peptide of claim 1.

5. A natriuretic composition comprising a peptide of claim 2 in combination with a pharmaceutically acceptable carrier.

6. A method lowering hypertension which comprises administering to a mammalian species a therapeutically active amount of a peptide of claim 2.

* * * * *